(12) United States Patent
Salahshoor Kordestani

(10) Patent No.: US 11,519,904 B2
(45) Date of Patent: Dec. 6, 2022

(54) INFECTION DETECTION DEVICE AND METHOD USING SAME

(71) Applicant: Soheila Salahshoor Kordestani, London (GB)

(72) Inventor: Soheila Salahshoor Kordestani, London (GB)

(*) Notice: Subject to any disclaimer, the term of this patent is extended or adjusted under 35 U.S.C. 154(b) by 246 days.

(21) Appl. No.: 16/920,662

(22) Filed: Jul. 4, 2020

(65) Prior Publication Data
US 2020/0355675 A1 Nov. 12, 2020

(51) Int. Cl.
*G01N 33/52* (2006.01)
*G01N 21/78* (2006.01)

(52) U.S. Cl.
CPC ........... *G01N 33/528* (2013.01); *G01N 21/78* (2013.01)

(58) Field of Classification Search
CPC .... G01N 33/528; G01N 33/523; G01N 21/78; C12Q 1/37; C12Q 1/04
See application file for complete search history.

(56) References Cited

U.S. PATENT DOCUMENTS

| | | | |
|---|---|---|---|
| 9,856,446 B2 | 1/2018 | Suslick | |
| 2011/0275112 A1* | 11/2011 | Sarver, Jr. | C12M 41/34 435/287.5 |
| 2012/0003685 A1* | 1/2012 | Kritzman | C12Q 1/04 435/287.7 |
| 2012/0028297 A1* | 2/2012 | Zook | C12Q 1/24 435/287.7 |
| 2019/0142642 A1* | 5/2019 | Burnet | A61B 5/445 600/362 |

OTHER PUBLICATIONS

Heinzle, A et al., "Novel protease-based diagnostic devices for detection of wound infection", Wound Repair and Regeneration, 21:482-9, (2013).

* cited by examiner

*Primary Examiner* — Jennifer Wecker
*Assistant Examiner* — Alea N. Martin
(74) *Attorney, Agent, or Firm* — Mehran Kasra

(57) ABSTRACT

The invention provides device and method for detecting infection in a body fluid, in particular in wound exudates and urine, based on protease activity. The device is founded on a detector consisting of one layer, which is an absorbent layer impregnated with a solution formed by dissolving a pH sensitive dye, such as bromothymol blue, in a gelatin solution. The method uses the device in form of a test strip for quick detection of an infection by observing a change in the color of the detector.

12 Claims, 2 Drawing Sheets

 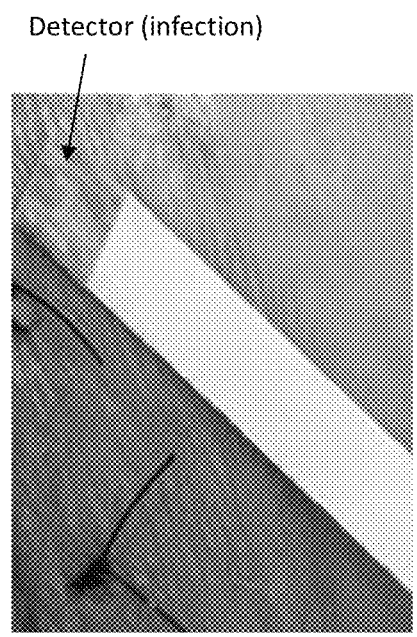
FIG. 2A  FIG. 2B

INFECTION DETECTION DEVICE AND METHOD USING SAME

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING SUBMITTED ELECTRONICALLY

Not Applicable

BACKGROUND

Field of the Invention

The present invention relates to a device comprising a detector for diagnosis of infection in body fluids or aqueous body tissues. In particular, the invention relates to a test strip and method for detection of infection in urine and wound fluid exudates.

Description of the Prior Art

As the percentage of the older adult population rises, so will the incidence and significance of chronic wounds and wound infections. Many of these wounds, including those related to chronic venous insufficiency, peripheral arterial disease, and pressure injuries or ulcers, rarely heal quickly or without complications such as infection.

The neutrophil population is a well-known marker for the diagnosis of wound infection. This marker increases immediately after bacterial entry and start of infection. The level of proteolytic enzymes, specifically Matrix metalloproteinases (MMPs), such as protease type A (MMP-2) and protease type B (MMP-9) will be increased by neutrophils' defensive activity, which is significantly different from non-infection state and can be used as an indicator for detection of infection.

MMP-2 (gelatinase A) and MMP-9 (gelatinase B) belong to the gelatinase subgroup and readily digest gelatins as one of their substrate (Malla et al., 2008; Xu et al., 2005). Due to the substrate (gelatin) reaction with the protease (MMPs), the level of proteolytic activity in a diagnostic system can be a marker for detecting infection in wounds that their healing is disrupted.

Another source of proteases in wounds is bacteria. In addition to stimulating protease production via activation of the immune system (neutrophils), some bacteria in wounds may themselves secrete proteases.

In the last decade, new techniques have been developed to improve wound infection detection by genotyping methods such as DNA microarray and multiplex real-time PCR (Thomsen et al., 2010; Tong et al., 2011). The disadvantages of these new techniques, especially those requiring culturing of biopsies, are that they are time consuming, have to be analyzed in a laboratory, and some tests are expensive or not commonly available. With the development of technology, researchers have designed methods aiming at a more effective detection of wound infection, based on electronic sensors that require complex instruments (Ciani et al, 2012; Sheybani and Shukla, 2017; Mannoor et al., 2010).

Another method of detecting wound infection is by determining the pH level of wound fluid exudates. Healthy, intact skin has a slightly acidic pH ranging from 4.0 to 6.0 (Sharpe et al., 2009). When a wound occurs, the skin's acidic milieu and pH is disrupted, exposing the more neutral pH 7.4 of the underlying tissue. Acute wounds have a more neutral pH. If however wound healing is delayed, then the pH will oscillate and become increasingly alkaline over time (Schneider et al., 2007). At this stage the wound is described as chronic and the synthesis of the extracellular matrix (ECM) molecules becomes impaired. Recordings of the chronic wound environment have been in the range of pH 7.15 to 8.9 (Gethin, 2007).

The effects of pH on some aspects of wound healing are known. These include the effects on matrix metalloproteinases (MMPs), tissue inhibitors of matrix metalloproteinases (TIMPs), immunological responses, and cellular activity (Woessner and Taplin, 1988).

It is reported that bacterial colonization may contribute to the shift toward an alkaline pH. Pathogenic bacteria have demonstrated a preference to a more alkaline environment to grow, and bacterial colonization and proliferation is encouraged at a higher pH. This causes a shift in pH, making the wound environment alkaline as it develops into a chronic wound (Gethin, 2007).

pH levels of an aqueous mater such as urine or wound exudates can be determined by a dye sensitive to a change in pH, such as bromothymol blue, commonly used for showing different alkaline environments.

Detection of bacterial growth and diagnosing infection in wound dressings, using bromothymol blue, was suggested in U.S. Pat. Nos. 9,499,852 and 8,871,464. In these patents gelatin was not used as a substrate.

U.S. Pat. No. 9,110,030 described how to detect wound infection by detecting the presence of gelatinases using a gelatinase assay and a reagent pad comprising a dried form of gelatin-coated nanoparticles. In this invention, a change in pH or use of bromothymol blue was not used for detection of wound infection.

U.S. Pat. Appl. Pub. No. 20180245124 A1 teaches bacteria identification and antimicrobial susceptibility test, wherein bromothymol blue can be used as the pH indicator in conjunction with a cultured bacteria growth media.

U.S. Pat. No. 9,856,446 teaches apparatus and method for detecting and identifying microorganisms, wherein gelatin growth medium was used for supporting growth of microorganisms to be detected and using different chemorresponsive dyes including bromothymol blue as a pH detector.

U.S. Pat. Appl. Pub. No. 20190142642 A1 describes a wound infection detection system based on wound dressing comprising a wound contacting layer and a reagent layer, wherein different gel-forming polymers were suggested for the wound contacting layer and different pH sensitive dyes, including bromothymol blue, was suggested for the reagent layer. However, no composition of a pH sensitive dye and gelatin in one layer was described.

In the wound infection detection systems as described above, the response time was not addressed. Most of them are based on a wound dressing structure comprising of many layers, which more likely have a longer response time than a single layer, or they need an extra step of culturing. Therefore, they may not be suitable for a point of care quick response testing.

Addressing the response time, Heinzle et al. (2013) developed a gelatinase-based device aiming for a fast detection of wound infection, using gelatin bids covalently bound to dies. Using their device, in an diagnostic experiment with infected wound fluid samples, an incubation time of 30 minutes was needed to produce a clearly visible dye release.

Urinary tract infections (UTIs) are another most commonly diagnosed and treated infection in patients presenting with both nonspecific and specific symptoms. Gold standard for diagnosing bacterial infections in the laboratory is urine culture that is labor-intensive and time-consuming and also shows high false-positive results due to contamination (Saadeh and Mattoo, 2011; Ottolini, 1995). The quick enzymatic methods using a dip stick including a pH sensitive dye also lack sensitivity (Khasriya et al., 2010). Given the problems with current testing techniques, developing alternative diagnostic assays is a high priority. In this case, quick and accurate detection of urinary tract infections (UTIs) may also be performed by using a pH sensitive dye in interaction with a gelatin substrate.

Considering the current devices and methods related to detection of infection in wounds and urine, there is still a need for advancement of sensors for point-of-care infection detection check, which are cost-efficient and can quickly detect infected wounds and urine.

SUMMARY OF THE INVENTION

It is the object of the present invention to provide an infection detection system which can operate rapidly, efficiently, and cheaply; thereby, overcoming the disadvantages of currently employed infection detection systems; such as using extra step of culturing or requiring manipulation of dressings or contact layers comprising of many parts. The infection detection system provided in this invention is based on protease activity in body fluids, such as wound fluid exudates and urine. The device is intended to diagnose wound and urine infections quickly with the ability to detect infection for all chronic wound, therefore, facilitating decision making for treatment and reducing the medical costs of unnecessary antibiotics and hospitalization.

The device includes a detector comprising an absorbent layer, wherein the absorbent layer is impregnated with a sensing solution containing gelatin and bromothymol blue. Bromothymol blue is selected as a pH sensitive dye. When the detector is exposed to an infected body fluid, the gelatinase in the body fluid, produced due to an infection, interacts with the gelatin in the sensing solution causing a change in the color of the bromothymol blue; therefore, changing the color the detector and indicating the existence of an infection according to the color observed.

Despite of its simplicity, the system and method of the invention, including the composition of the gelatin and bromothymol blue in one solution (sensing solution) placed in one layer (absorbent layer), have provided advantages and new features including the following:

(1) The device can diagnose wound and urine infections within about 60 seconds, with high sensitivity and specificity.

(2) There is no requirement for special instrumentation and no need for colony isolation and culture enrichment.

BRIEF DESCRIPTION OF THE FIGURES

A fuller understanding of the nature and objects of the present invention will become apparent upon consideration of the following detailed description taken in connection with the accompanying drawings, wherein:

FIGS. 2A-2B are grayscale photographs showing examples of a test strip in detecting wound infection according to the present invention. FIG. 2A is a grayscale photograph showing no change in the color of the detector indicating no infection. FIG. 2B is a grayscale photograph showing change in the color of the detector indicating infection.

DETAILED DESCRIPTION OF THE PREFERRED EMBODIMENTS

Figure 1:
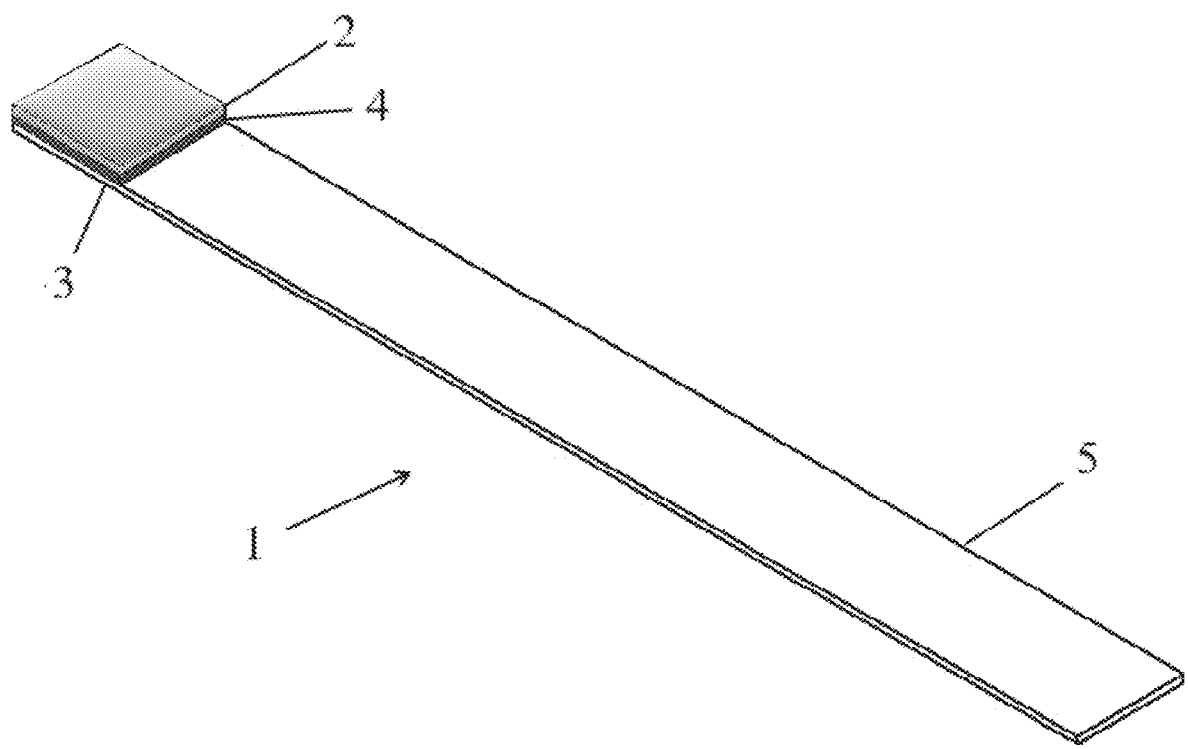
FIG. 1 is a perspective drawing of a test strip in accordance with the preferred embodiment of the present invention.

Unless defined otherwise, all publications, patent applications, patents, and other references mentioned herein are incorporated by reference in their entirety. In case of conflict, the present specification, including definitions, will control.

As used herein, the concentration of a solute in a solution is expressed as the percent weight per volume (w/v). Percent weight per volume (w/v) is defined as the grams of solute in 100 milliliters (mL) of solution.

The present invention relates to a device, preferably in form of a test strip that can quickly detect infection in a body fluid within a time period of less than or equal 60 seconds.

In this invention we describe (1) construction of a device, preferably in form of a test strip for detecting infection in a body fluid; (2) construction and preparation process of a detector for said device; and (3) method of using said device for detecting infection in a body fluid. In the section of examples, a test strip (Example 1) and the use of the test strip for detecting infections in wounds (Example 2) and urine (Example 3) are illustrated.

(1) Construction of the device in form of a test strip: FIG. 1 shows a test strip 1, which includes a detector 2, a base layer 3, and an adhesive layer 4. The base layer 3 has a testing side at one end, where the detector 2 is attached, and a grip side 5 at the other end for holding and manipulating the test strip 1. The adhesive layer 4 is disposed between the detector 2 and the base layer 3, attaching the detector 2 to the base layer 3. The base layer 3 is preferably made of a cardboard, laminated cardboard, or plastic, more preferably of a cardboard. The adhesive layer 4 is preferably a double sided adhesive adhering to the detector 2 at one side and to the base layer 3 at its opposite side. The color of the base layer 3 is preferably chosen based on increasing the color contrast between the base layer 3 and the detector 2, for example, white color. It will be understood that the term "strip" as used herein, is not limited to an elongated strip-like shape, for the reason that such a shape is immaterial to the invention.

(2) Construction and preparation process of the detector: The detector 2 (FIG. 1) consists of an absorbent layer impregnated with a sensing solution, wherein the sensing solution is prepared by dissolving bromothymol blue in a gelatin solution. Therefore, the detector has the gelatin as a substrate and the bromothymol blue as a pH sensitive dye, both in one layer. For this purpose, different dyes were tested in different concentrations, among which bromothymol blue showed the best performance in combination with gelatin in terms of homogeneity of the sensing solution and a short incubation time for producing a clearly visible change in color.

In a preferred embodiment, wherein the absorbent layer is a filter paper, the detector 2 is prepared comprising the steps:

(a) preparing the gelatin solution with a gelatin concentration of about 3% (w/v) to about 5% (w/v), more preferably 3% (w/v), by dissolving gelatin powder in a sterile water, preferably distilled water; for example, a gelatin solution of 3% (w/v) gelatin is prepared by dissolving 3 gram of gelatin in distilled water having a gelatin concentration of 3 gram per 100 mL of the gelatin solution;
(b) dissolving bromothymol blue powder with a concentration of about 0.1% (w/v) to about 0.3% (w/v), more preferably 0.1% (w/v), in the gelatin solution forming the sensing solution; for example, a sensing solution of 3% (w/v) gelatin and 0.1% (w/v) bromothymol blue is prepared by dissolving 0.1 gram of bromothymol blue in the 3% (w/v) gelatin solution, having a bromothymol blue concentration of 0.1 gram per 100 mL of the sensing solution;
(c) impregnating the filter paper (absorbent layer) after the sensing solution reaches the room temperature, by immersing the filter paper in the sensing solution for a period of about 1 to 3 minutes; and
(d) letting the filter paper, impregnated with the gelatin and bromothymol blue, out of the sensing solution to dry at room temperature, forming the detector with an initial color of yellow.

In the disclosed compositions, water suitable for use in the disclosed compositions is preferably distilled water, deionized water, or de-mineralized water; the bromothymol blue powder preferably has a molar weight of about 624.40 g/mole and a bulk density of about 450 kg/m$^3$ (Sigma-Aldrich); and the gelatin powder is gelatin from bovine skin, Type B (Sigma-Aldrich).

The concentrations of gelatin and bromothymol blue in the sensing solutions were determined in an experimental study by placing detectors of different concentrations of gelatin and bromothymol blue in contact with media of different pH values. The concentrations of gelatin and bromothymol blue in the sensing solution were selected based on producing a detectable change in the color of the detector from yellow to green within a short period of time of less or equal to 60 seconds. The selected concentrations were determined to be from about 3% (w/v) to about 5% (w/v) for gelatin and about 0.1% (w/v) to about 0.3% (w/v) for bromothymol blue. In this case, a composition of about 3% (w/v) gelatin and about 0.1% (w/v) bromothymol blue at a pH of about 6.4 had the best performance and was used in making the test strip of example 1.

(3) Method of using the device: Detection of infection in a body fluid using the device comprises the following steps:
(a) place the detector of the device, initially having a yellow color, in contact with a body fluid, such as urine or wound fluid exudates;
(b) wait for about 60 seconds, or until the color of the detector stabilizes; and
(c) observe the detector color; if there is no change in the initial yellow color, there is no infection (FIG. 2A); if the color is changed to green, there is an infection (FIG. 2B). In grayscale photographs (FIGS. 2A and 2B), the green color appears darker than the yellow color.

The present invention will be illustrated in more details with reference to examples 1 to 3, showing the fabrication of a test strip (Example 1) used in an infection detection kit for detection of infection in a body fluid, such as wounds fluid exudates (Example 2) and urine (Example 3). In examples 2 and 3, the results of the test strip was validated by comparing the results of test strip tests with those of their corresponding standard laboratory culture tests. These examples are presented only for illustrative purpose and are not intended to limit the scope of the present invention in any way.

Example 1

Fabrication of a Test Strip

In accordance with a preferred embodiment shown in FIG. 1, a test strip 1 was manufactured using a detector 2. The detector consisted of a filter paper impregnated with a sensing solution including 3% (w/v) gelatin and 0.1% (w/v) bromothymol blue. A cardboard was used as the base layer 3, and a double sided adhesive as the adhesive layer 4. The filter paper (Whatman® qualitative filter paper, Grade 1) had a thickness preferably of about 0.26 mm, which was cut in shape of a square of about 7 mm length and 7 mm width. The base layer 3 was made of a cardboard with a thickness preferably of about 0.5 to 1 mm, which was cut into a rectangle of 70 mm length and 7 mm width. The adhesive layer 4 (Nano Tape, adhesive type: Cellulose) was a double sided adhesive cut into a rectangle of 7 mm length and 7 mm width. The impregnated filter paper (detector 2) was then attached on the cardboard (base layer 3) using the double sided adhesive (adhesive layer 4). Plurality of the test strip 1 along with a colorimetric scale were used as an infection detection kit for wounds and urine as illustrated in examples 2 and 3.

Example 2

Detection of Infection in Wounds

Fifty-one patients with chronic and acute wounds, not receiving antibiotic treatment within 7 days before the tests, were investigated. Wounds washed with sterile saline and then superficially contacted with the detector of the test strip. In case of an infection, upon contact, the color of the detector start changing rapidly from yellow to green and stabilizes within about 60 seconds. Wound swab cultures were collected and laboratory results were used as control group. Wounds with a growth of ≥10$^5$ colony forming unit (CFU) per ml was considered to have a positive culture (Lindsay et al., 2017). Among the 51 patients, 37 were found to have wound infection by both the laboratory and test strip. As was verified by laboratory tests, *Staphylococcus aureus* and Gram-positive cocci were the most prevalent pathogenic yield from the cultures. Other bacteria detected by cell culture laboratory and were involved with the infections detected by the test strip were: *Acinetobacter baumannii*, *Acinetobacter baumannii* & *Candid*, *Klebsiella pneumonii*, Gram+cocci, Yeast, *Staphylococcus aureus* Coagulase-positive, *Staphylococcus aureus* Coagulase-negative, *Staphylococcus aureus* β-hemolytic, *Corynebacterium diphtheria*, *Escherichia coli*, Gram-positive cocci, Gram-positive coccobacilli, Gram-negative cocci, Gram-negative bacilli, Gram-negative diplococcic, Gram-negative coccobacilli, Gram-positive & gram-negative cocci, and Mixed bacteria.

FIGS. 2A and 2B are grayscale photographs showing examples of the test strip response for detection of infection in wounds. The test strip shown in FIG. 2A showed no change in initial yellow color of its detector indicating no infection; and the detector of the test strip shown in FIG. 2B changed its color to green indicating infection.

The accuracy, sensitivity and specificity of the test strip for detection of wound infection, calculated against the wound culture, were 96%, 97.4% and 92.3% respectively. All the results were significant ($p \leq 0.01$). As described in the literature (Van Stralen et al., 2009), accuracy is the ability to differentiate the infected patient and non-infected patient cases correctly; sensitivity is the ability to determine the infected patient cases correctly; and specificity is ability to determine the non-infected patient cases correctly.

Example 3

Detection of Infection in Urine

In this study, urine specimens of 50 patients, with no antibiotic treatment, were examined for the urinary tract infections (UTIs), based on the presence of MMPs activity as an indicator of bacteriuria. The validity of the test strip results of patients with or without clinical symptoms of urinary tract infection (UTIs) was investigated by comparing the test strip results with those of their corresponding urine culture test as a control group.

Among the 50 patients, 3 were found to have UTIs by both the laboratory and the test strip. The accuracy, sensitivity, and specificity for the strip calculated against the urine culture for the diagnosis of UTIs, were 98%, 100%, and 97.9% respectively. All the results were significant ($p \leq 0.01$).

The bacteria involved with the urine infections that were detected by the strip and cell culture tests were *Escherichia coli* and *Proteus vulgaris*, where *Escherichia coli* was the most prevalent pathogenic yield from the cultures.

The results indicated that using the test strip of the present invention can provide a fast, accurate and cost-effective screening method for bacteriuria; and it is able to rule out UTIs. This can lead to a substantial reduction of urine cultures. It also demonstrated that this method predicts negative cultures accurately.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

REFERENCES

US Patent Documents

U.S. Pat. No. 8,871,464 October 2014 Booher
US 20180245124 A1 August 2018 Bork
US 20190142642 A1 May 2019 Burnet et al.
U.S. Pat. No. 9,499,852 November 2016 Jenkins et al.
U.S. Pat. No. 9,110,030 August 2015 Kerschensteiner
U.S. Pat. No. 9,856,446 January 2018 Suslick et al.

OTHER PUBLICATIONS

Ciani I, et al., "Development of immunosensors for direct detection of three wound infection biomarkers at point of care using electrochemical impedance spectroscopy", Biosensors and Bioelectronics, 31:413-418, (2012).
Gethin G., "The significance of surface pH in chronic wounds", Wounds, 3:52-55, (2007).
Heinzle A et al., "Novel protease-based diagnostic devices for detection of wound infection", Wound Repair and Regeneration, 21:482-9, (2013).
Khasriya R et al., "The inadequacy of urinary dipstick and microscopy as surrogate markers of urinary tract infection in urological outpatients with lower urinary tract symptoms without acute frequency and dysuria", The Journal of urology, 183:1843-7, (2010).
Lindsay et al., "The detrimental impact of extracellular bacterial proteases on wound healing", International wound journal," 14:1237-1247, (2017).
Malla N et al., "Interaction of pro-matrix metalloproteinase-9/proteoglycan heteromer with gelatin and collagen", Journal of Biological Chemistry, 283:13652-65. (2008).
Mannoor M S, et al., "Electrical detection of pathogenic bacteria via immobilized antimicrobial peptides", Proceedings of the National Academy of Sciences, 107: 19207-19212, (2010).
Ottolini M C et al., "Relationship of asymptomatic bacteriuria and renal scarring in children with neuropathic bladders who are practicing clean intermittent catheterization", J pediatrics, 127:368-372, (1995).
Saadeh S A and Mattoo T K. "Managing urinary tract infections", Pediatric Nephrology, 26:1967-76. (2011).
Schneider L A, et al., "Influence of pH on wound-healing: a new perspective for wound-therapy?", Arch Dermatol Res, 298:413-20. (2007).
Sharpe J R, et al., "The effect of pH in modulating skin cell behaviour", Br J Dermatology. 161:671-3, (2009).
Sheybani R and Shukla A, "Highly sensitive label-free dual sensor array for rapid detection of wound bacteria", Biosensors and Bioelectronics", 92:425-433, (2017).
Thomsen T R, et al., "The bacteriology of chronic venous leg ulcer examined by culture-independent molecular methods", Wound Repair Regen, 18: 38-49, (2010).
Tong J, et al., "Application of quantitative real-time PCR for rapid identification of *Bacteroides fragilis* group and related organisms in human wound samples", Anaerobe, 17: 64-8, (2011).
Van Stralen K J, et al., "Diagnostic methods I: sensitivity, specificity, and other measures of accuracy", Kidney international, 75:1257-63, (2009).
Woessner J F and Taplin C J, "Purification and properties of a small latent matrix metalloproteinase of the rat uterus", Journal of Biological Chemistry", 263:16918-25. (1988).
Xu X, et al., "Functional basis for the overlap in ligand interactions and substrate specificities of matrix metalloproteinases-9 and -2", Biochemical Journal, 392(1):127-34, (2005).

I claim:

1. A device for point of care detection of infection in a body fluid, the device comprising a detector, wherein the detector comprises an absorbent layer impregnated with a sensing solution, wherein the sensing solution contains gelatin and bromothymol blue, and wherein the detector is made comprising the steps:
   (a) preparing a gelatin solution;
   (b) dissolving bromothymol blue in the gelatin solution forming the sensing solution; and
   (c) impregnating the absorbent layer with the sensing solution.

2. The device as claimed in claim 1, wherein the impregnation of the absorbent layer in step (c) comprises immersing the absorbent layer in the sensing solution, taking the impregnated absorbent layer out of the sensing solution, and letting the impregnated absorbent layer to dry at room temperature to yield the detector.

3. A device as claimed in claim 1, wherein the concentration of gelatin in the gelatin solution is about 3% (w/v) to about 5% (w/v) and the concentration of the bromothymol blue in the sensing solution is about 0.1% (w/v) to about 0.3% (w/v).

4. A device as claimed in claim 3, wherein the concentration of gelatin in the gelatin solution is about 3% (w/v) and the concentration of bromothymol blue in the sensing solution is about 0.1% (w/v).

5. A device as claimed in claim 1, the device further comprises a base layer and an adhesive layer forming a test strip, the test strip having a grip region at one end and a testing region at the other end, and the adhesive layer is disposed between the detector and the base layer attaching the detector to the base layer at the testing region.

6. The test strip of claim 5, wherein the concentration of gelatin in the gelatin solution is about 3% (w/v) and the concentration of bromothymol blue in the sensing solution is about 0.1% (w/v), and wherein the absorbent layer is a filter paper.

7. A method for detection of infection in a body fluid using the test strip of claim 6, the method comprising the steps of:
   (a) placing the detector of the test strip in contact with a body fluid;
   (b) waiting for a response time period; and
   (c) visually inspecting the detector for a color change.

8. The method of claim 7, wherein the color change of the detector is a yellow to green color change when indicating an infection.

9. The method of claim 7, wherein the response time period is less than or equal 60 seconds.

10. The method of claim 7, wherein the body fluid is urine or wound fluid exudates.

11. A device for point of care detection of infection in a body fluid, the device comprising a detector, wherein the detector comprises an absorbent layer impregnated with a sensing solution, wherein the sensing solution contains gelatin and a pH indicator dye, and wherein the detector is made comprising the steps:
   (a) preparing a gelatin solution;
   (b) dissolving the pH indicator dye in the gelatin solution forming the sensing solution; and
   (c) impregnating the absorbent layer with the sensing solution.

12. A device as claimed in claim 11, the device further comprises a base layer and an adhesive layer forming a test strip, the test strip having a grip region at one end and a testing region at the other end, and the adhesive layer is disposed between the detector and the base layer attaching the detector to the base layer at the testing region.

* * * * *